United States Patent [19]

Cassidy et al.

[11] 4,201,864
[45] May 6, 1980

[54] OXY-ALKYLAMINO ACIDS AND ESTERS

[75] Inventors: Frederick Cassidy, Harlow; Gordon Wootton, Sawbridgeworth, both of England

[73] Assignee: Beecham Group Limited, Great Britain

[21] Appl. No.: 962,875

[22] Filed: Nov. 22, 1978

Related U.S. Application Data

[62] Division of Ser. No. 732,726, Oct. 15, 1976, Pat. No. 4,138,407.

[30] Foreign Application Priority Data

Oct. 25, 1975 [GB] United Kingdom ............... 43990/75
May 22, 1976 [GB] United Kingdom ............... 21278/76

[51] Int. Cl.² ............................................. C07C 101/20
[52] U.S. Cl. ................................ 560/39; 560/21; 560/22; 560/121; 560/125; 560/156; 560/170; 560/250; 560/253; 560/254; 560/255; 562/435; 562/437; 562/444; 562/503; 562/507; 562/564; 562/568

[58] Field of Search ................. 560/21, 22, 39, 121, 560/125, 156, 170, 250, 253, 254, 255; 562/435, 437, 444, 503, 507, 568, 564

[56] References Cited

U.S. PATENT DOCUMENTS

2,582,257  1/1952  Jones .................................... 260/404
3,873,566  3/1975  Scribner .............................. 548/367

OTHER PUBLICATIONS

Tancheck et al., Chem. Absts., 81, 136 472(k) (1974).
Singerman et al., Chem. Absts., 65, 5523(b) (1966).
Cassidy et al., Chem. Absts., 85, 192576(s) 1976.
Bolliger et al. Tet. Letters, 2931 (1975).

*Primary Examiner*—Bernard Helfin
*Assistant Examiner*—G. T. Breitenstein
*Attorney, Agent, or Firm*—Jacobs & Jacobs

[57] ABSTRACT

Compounds of formula (I):

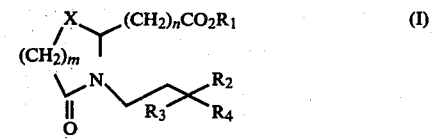

wherein: m is 1 or 2; n is 4 to 8; X is CO, protected CO, or CROH wherein R is hydrogen or $C_{1-4}$ alkyl and wherein the OH moiety may be protected; $R_1$ is hydrogen or $CO_2R_1$ represents an ester group in which the $R_1$ moiety contains from 1 to 12 carbon atoms; $R_3$ is hydroxy, or protected hydroxy; $R_2$ and $R_4$ are separately hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl $C_{1-6}$ alkyl, any of which phenyl or naphthyl moieties may be substituted by one or more halogen, trifluoromethyl, $C_{1-6}$ alkyl, $C_{1-6}$ alkoxy or nitro groups; or $R_2$ and $R_4$ taken with the carbon atom to which they are joined represent a $C_{5-8}$ cycloalkyl group; and salts thereof; except that when one of $R_2$ and $R_4$ is hydrogen or $C_{1-4}$ alkyl then the other of $R_2$ and $R_4$ cannot be hydrogen or $C_{1-9}$ alkyl; have useful pharmacological properties including antigastric secretion, bronchodilator and platelet aggregation inhibition activities.

12 Claims, No Drawings

OXY-ALKYLAMINO ACIDS AND ESTERS

CROSS-REFERENCE

This is a division of Ser. No. 732,726 filed Oct. 15, 1976, now U.S. Pat. No. 4,138,407.

This invention relates to novel compounds having pharmaceutical activity, to a process for their preparation, to intermediates useful in that process, and to pharmaceutical compositions containing them.

More specifically the invention relates to cyclic amides in which the nitrogen atom is substituted by an aliphatic or aliphatic-aromatic group and one α-carbon atom is substituted by an aliphatic group.

Natural prostaglandins and analogues thereof are known to possess a wide variety of pharmacological activities.

Offenlegungsschrift No: 2323193 discloses that pyrazolidine derivatives of the formula (I)':

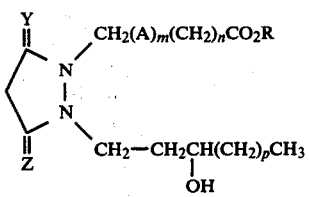

wherein A is CH=CH or C≡C; R is H, an alkali metal, an amine salt, or an ≯ 12C hydrocarbon or chlorohydrocarbon residue; m is 0 or 1; n is 0–6; p is 0–6; and Y and Z are O or H₂ except that Y and Z are not both 0; have similar biological properties to the prostaglandins or are antagonists of prostaglandins.

A paper by Bolliger and Muchowski (Tet. Letters, 1975, 2931) describes the preparation of 11-desoxy-8-azaprostaglandin E₁, but states only that one epimer thereof was more active in several biological assays than the other epimer.

Copending U.S. Patent Application No. 632975 discloses that compounds of the formula (I)":

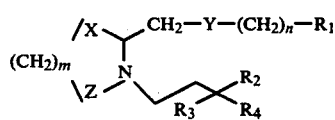

wherein:
X is CO, protected CO, CROH in which R is hydrogen or $C_{1-4}$ alkyl and in which the OH moiety may be protected;
Y is CH₂CH₂ or CH=CH; Z is CO or CH₂; n is 1 to 8; m is 1, 2 or 3; R₁ is hydrogen, CH₂OH, CH₂OH in which the OH moiety is protected, CO₂W wherein W is hydrogen or CO₂W represents an ester group in which the ester moiety contains from 1 to 12 carbon atoms, or CONH₂; R₂ is hydrogen, $C_{1-4}$ alkyl, or taken together with R₃ and the carbon atom to which it is attached represents a carbonyl group; R₃ is hydrogen, hydroxy or protected hydroxy; R₄ is hydrogen or $C_{1-9}$ alkyl; and salts thereof; have useful pharmacological activity.

This subject matter was first published in Belgium Pat. No. 835989 on the 26th May 1976, a date later than the filling date of the two U.K. Applications Nos: 43990/75 and 21278/76 from which priority has been claimed for the present invention.

A novel class of compounds having useful pharmacological activity has now been discovered, which compounds are structurally distinct from the prior art referred to above.

The present invention provides a compound of the formula (I):

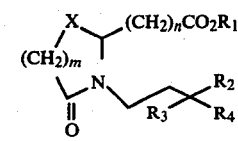

wherein:
m is 1 or 2;
n is 4 to 8;
X is CO, protected CO, or CROH wherein R is hydrogen or
$C_{1-4}$ alkyl and wherein the OH moiety may be protected;
R₁ is hydrogen or CO₂R₁ represents an ester group in which the R₁ moiety contains from 1 to 12 carbon atoms;
R₃ is hydroxy, or protected hydroxy;
R₂ and R₄ are separately hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl $C_{1-6}$ alkyl, any of which phenyl or naphthyl moieties may be substituted by one or more halogen, trifluoromethyl, $C_{1-6}$ alkyl, $C_{1-6}$ alkoxy or nitro groups; or R₂ and R₄ taken with the carbon atom to which they are joined represent a $C_{5-8}$ cycloalkyl group; and salts thereof; except that when one of R₂ and R₄ is hydrogen or $C_{1-4}$ alkyl then the other of R₂ and R₄ cannot be hydrogen or $C_{1-9}$ alkyl.

Suitably m is 1 and n is 5, 6 or 7, preferably 6.

Suitable protected hydroxyl groups CROH and R₃ include readily hydrolysable groups such as acylated hydroxy groups in which the acyl moiety contains 1 to 4 carbon atoms, for example the acetoxy group; and hydroxy groups etherified by readily removable inert groups such as the benzyl or like groups. Preferably R₃ is hydroxy, and the hydroxy moiety in CROH is unprotected.

X may be a protected CO group. Suitable examples of such protected CO groups X include groups formed by conventional carbonyl addition and condensation reactions such as ketals, thioketals, hemithioketals, oximes, semicarbazones, hydrazones and the like. Of such groups often the ketal type derivatives will be most useful, for example when X is a group

Examples of suitable groups X include CO, CHOH, C(CH₃)OH and C(C₂H₅)OH.

Preferably X is CO, CHOH or C(CH₃)OH, most preferably CO.

R₁ is hydrogen or CO₂R₁ represents an ester group in which the R₁ moiety contains from 1 to 12 carbon atoms. Examples of R₁ include hydrogen, methyl, ethyl, propyl, butyl, phenyl, benzyl, toluyl, and the like, while normally hydrogen or $C_{1-4}$ alkyl groups are preferred.

Suitable groups $R_4$ when $R_4$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example $R_4$ may be a group $CH_2R_5$, $CH(CH_3)R_5$ or $C(CH_3)_2R_5$, wherein $R_5$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_5$ and $C(CH_3)_2R_5$ wherein $R_5$ is straight chain butyl, pentyl and hexyl.

When $R_4$ is or contains a $C_{5-8}$ cycloalkyl moiety, the moiety is suitably a cyclohexyl moiety. Examples of suitable $C_{1-6}$ alkyl moieties when $R_4$ is a $C_{5-8}$ cycloalkyl-$C_{1-6}$ alkyl group include methyl, ethyl, propyl, butyl and amyl.

Examples of suitable groups $R_4$ when $R_4$ is an aryl group as previously defined include phenyl, phenylmethyl, phenylethyl, phenyl, n-propyl, phenyl n-butyl, naphthyl, naphthylmethyl, naphthylethyl, naphthyl n-propyl, and naphthyl-n-butyl, and such groups branched in the alkyl moiety by one or two methyl groups (at the same or different carbon atoms). These groups may be substituted in the phenyl or naphthyl moiety by normally one, two or three groups selected from these substituent groups listed herein before. Examples of suitable substituent groups include fluorine, chlorine and bromine atoms and $CF_3$, methyl, ethyl, n- and iso-propyl, methoxy, ethoxy, n- and iso-propoxy and nitro groups. Preferably the aryl moieties when substituted by such groups will be mono- or di- substituted.

Particularly suitable values for $R_2$ are hydrogen, $C_{1-4}$ alkyl and phenyl, for example hydrogen, methyl, ethyl and phenyl. Of these groups preferred groups include methyl and ethyl.

Otherwise $R_2$ can suitably represent groups such as those described above as suitable and preferred groups for $R_4$.

Also, $R_2$ and $R_4$ taken with the carbon atom to which they are joined can represent a $C_{5-8}$ cycloalkyl group, such as the cyclohexyl group.

The compounds of the formula (I) may form conventional acid salts when $R_1$ is hydrogen. Such salts include those with alkali and alkaline earth metals, suitably sodium and potassium, and ammonium and substituted ammonium salts.

A group of compounds within the compounds of the formula (I) as defined are those wherein X is CO, or CROH wherein R is hydrogen or $C_{1-4}$ alkyl and wherein the OH moiety may be protected; $R_2$ is hydrogen, $C_{1-4}$ alkyl or phenyl; and $R_4$ is hydrogen, $C_{1-9}$ alkyl, phenyl, phenyl $C_{1-4}$ alkyl, naphthyl, naphthyl $C_{1-4}$ alkyl, any of which phenyl or naphthyl moieties may be substituted by one or more halogen, trifluoromethyl, $C_{1-6}$ alkyl, $C_{1-6}$ alkoxy or nitro groups; except that when $R_2$ is hydrogen or $C_{1-4}$ alkyl, $R_4$ must be other than hydrogen or $C_{1-9}$ alkyl; and salts thereof.

One particularly suitable sub-group of compounds within such compounds of the formula (I) include those of the formula (II):

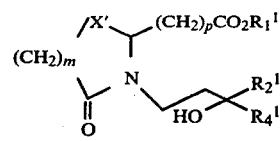

wherein:
m is as defined in formula (I);
p is 6 or 8;
X' is CO, CHOH or $C(CH_3)OH$;
$R_1{}^1$ is hydrogen or $C_{1-4}$ alkyl;
$R_2{}^1$ is hydrogen, methyl or ethyl; and
$R_4{}^1$ is a group of formula (III):

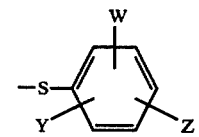

wherein S is a bond, or a $C_{1-6}$ alkylene group which maybe straight chain or branched by one or two methyl groups at the same or different carbon atoms; and W, Y and Z are each hydrogen or fluorine, chlorine or bromine atoms, or $CF_3$, methyl, ethyl, n- or iso-propyl, methoxy, ethoxy, n- or iso-propoxy or nitro groups; and salts thereof.

Often S will be a group $—(CH_2)_q—$ wherein q is 0 to 4.

In formula (II) m is most suitably 1, p is most suitably 6, X' is most suitably CO, and $R_2{}^1$ is most suitably methyl or ethyl. Also, W is most suitably hydrogen.

A second interesting sub-group of compounds within such compounds of formula (I) include those of formula (IV):

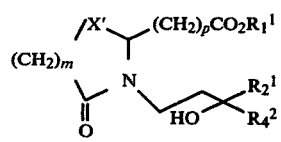

wherein m, p, X', $R_1{}^1$ and $R_2{}^1$ are as defined in formula (II), and $R_4{}^2$ is a group of formula (V):

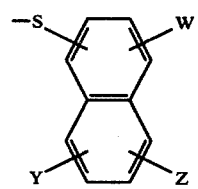

wherein S, W, Y and Z are as defined in formula (III); and salts thereof.

Often S will be a group $—(CH_2)_q—$ wherein q is 0 to 4.

In formula (IV) m is most suitably 1, p is most suitably 6, $X^1$ is most suitably CO and $R_2{}^1$ is most suitably methyl or ethyl.

A third sub-group of compounds within such compounds of formula (I) of particular interest are those of formula (VI):

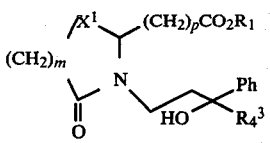

(VI)

wherein m, p, $X^1$ and $R_1^1$ are as defined in formula (II), and $R_4^3$ is a group of formula (III), a group of formula (V) or a $C_{4-9}$ alkyl group; and salts thereof.

The most suitable values for m and p in formula (VI) are 1 and 6 respectively, and $X^1$ is most suitably CO.

When $R_4^3$ is a $C_{4-9}$ alkyl group, suitable and preferred straight chain and branched groups $R_4^3$ include those previously described as suitable and preferred for the group $R_{43}$ when $R_4$ is $C_{4-9}$ alkyl group. Such preferred groups $R_4^3$ include straight chain pentyl, hexyl and heptyl, and of these normally the most useful is straight chain hexyl. Other preferred groups $R_4^1$ include $CH(CH_3)R_5^1$ and $C(CH_3)_2R_5^1$ wherein $R_5^1$ is straight chain butyl, pentyl or hexyl.

A fourth sub-group of compounds that is within formula (I) is of formula (VII):

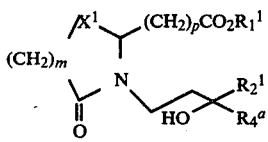

(VII)

wherein:
p,m,$X^1$, $R_1^1$ and $R_2^1$ are as defined in formula (II); and $R_4^a$ is a group of formula (VIII):

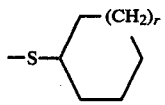

(VIII)

wherein S is as defined in formula (III) and r is 0 to 3; and salts thereof.

Often S will be a group $-(CH_2)_q-$ wherein q is 0 to 6.

In formula (VII) we prefer that p is 6. Most suitably $X^1$ is CO, $R_2^1$ is methyl or ethyl, and m is 1.

A fifth sub-group of compounds within formula (I) of interest is of formula (IX):

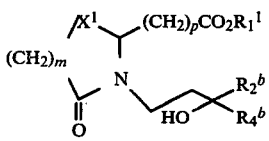

(IX)

wherein: p, m, $X^1$ and $R_1^1$ are as defined in formula (II); $R_2^b$ and $R_4^b$ are separately $C_{5-9}$ alkyl, or groups of formula (III), (V) or (VIII) as defined; or $R_2^b$ and $R_4^b$ taken together with the carbon atom to which they are joined represent $C_{5-8}$ cycloalkyl; and salts thereof.

In formula (IX) we prefer that p is 6. Most suitably $X^1$ is Co and m is 1.

Compounds of the formula (II), (IV), (VI), (VII), or (IX) as defined, but wherein $X^1$ is a protected CO group, are also of particular utility.

The compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

The invention also provides a process for the preparation of the compounds of the formula (I), which process comprises decarboxylating a compound of the formula (X):

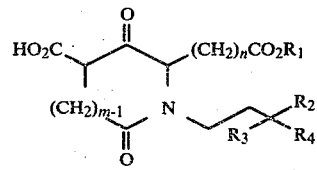

(X)

wherein m, n, $R_1$, $R_2$, $R_3$ and $R_4$ are as defined in formula (I), to yield a compound of the formula (I) wherein X is CO; and thereafter if desired protecting X, or converting X in the thus formed compound to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety.

The decarboxylation reaction may be brought about under basic, acid or neutral conditions in conventional manner. For example when m=1 the reaction is conveniently effected by leaving the chosen compound of the formula (X) in an inert solvent, for example overnight.

After the reaction $R_1$ may be varied by conventional de-esterification and/or esterification reactions. Similarly protected CROH and $R_3$ hydroxy moieties may be deprotected by conventional methods. For example, when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I).

The conversion of a compound of the formula (I) wherein X is CO to the corresponding compound wherein X is protected CO may be carried out under conventional reaction conditions for, for example, carbonyl addition and condensation reactions.

The conversion of a compound of the formula (I) wherein X is CO to the corresponding compound wherein X is CHOH may be carried out by conventional methods for reducing a ketone to an alcohol, for example by sodium borohydride reduction.

The conversion of a compound of the formula (I) wherein X is CO to the corresponding compound wherein X is CROH in which R is $C_{1-4}$ alkyl may be carried out by conventional Grignard or alkyl metal, (suitably alkyl lithium) reactions.

When $R_1$ is hydrogen, salts of compounds of the formula (I) may be prepared in conventional manner, for example by reacting the chosen compound of the formula (I) with the required base.

It is frequently convenient however to generate the desired compound of the formula (I) directly from an ester of the formula (XI), and often this will in fact be the preferred route:

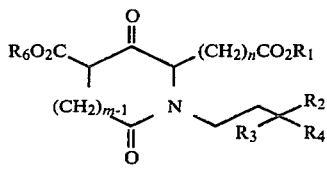

(XI)

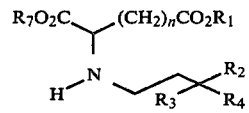

(XIII)

where $CO_2R_6$ is a conventional ester group. In such a case $R_6$ is preferably a benzyl group or a lower alkyl group such as ethyl or the like. Thus treatment of a compound of the formula (XI) with, for example, lithium iodide dihydrate and collidine in anydrous solvents brings about simultaneous de-esterification and decarboxylation. In cases where m=1, the compound of formula (XI) can be de-esterified and decarboxylated by leaving the compound standing in an inert solvent, e.g. overnight, or by heating the compound alone or in a high boiling solvent such as toluene or xylene.

It will be appreciated that compounds of the formulae (X) and (XI) are useful intermediates and as such form a useful aspect of this invention.

The compounds of formula (XI) may be prepared by the ring closure of the corresponding diester of formula (XII):

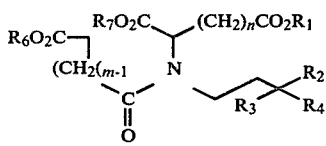

(XII)

wherein m, n, $R_1$, $R_2$, $R_3$, and $R_4$ are as defined in formula (I), $R_6$ is as defined in formula (XI), and $R_7$ is a group such that $CO_2R_7$ is an ester group.

In the process of the invention the group $CO_2R_1$ in the intermediates of formula (X), (XI) and (XII) will normally represent an ester group, and if acids of the formula (I) (wherein $R_1$ is hydrogen) are required they will be obtained by de-esterification of the corresponding compound of the formula (I) wherein $CO_2R_1$ is an ester group. Usually the ester group $CO_2R_7$ in formula (XII) will be the same ester group as $CO_2R_1$, and for the sake of convenience the ester group $CO_2R_6$ will also normally be the same ester group as $CO_2R_1$. The ester groups $CO_2R_1/R_6/R_7$ are suitably $C_{1-4}$ alkyl esters such as methyl and ethyl esters.

Generally, the ring closure takes place in a dry organic solvent using a strong base such as sodium hydride or sodium ethoxide (or other $-OR_6$ or $-OR_7$ group) to bring about the initial proton abstraction from the α-methylene group.

It has been found that sodium ethoxide in benzene, or potassium t-butoxide in toluene, benzene or hexamethylphosphoramide give good results.

Compounds of formula (XII) are novel useful intermediates and as such, from an aspect of this invention.

Compounds of formula (XII) may be prepared by the esterification of a corresponding acid or by the reaction of a compound of the formula (XIII):

with a reactive acylating derivative of an acid of the formula $$HO_2C-(CH_2)_m-CO_2H \quad (XIV)$$

or an ester thereof.

Suitable reactive acylating derivatives include (a) compounds of the formula (XV):

$$R_6O_2C-(CH_2)_m-CO-Z \quad (XV)$$

where Z is a readily displaceable group such as Cl, Br, $OSO_2CH_3$, $OSO_2C_6H_4CH_3$, $OCO(CH_2)_mCO_2R_6$ or like, (b) compounds of the formula (XV) wherein Z is OH in the presence of dicyclohexyl carbodiimide as a condensing agent, and (c) a cyclic anhydride such as:

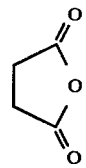

The reaction of the compound (XIII) with the compound (XIV) and (XV) occurs under conventional acylation conditions.

The novel substituted amino acids (XIII) are highly useful intermediates and form an important aspect of the present invention.

The compounds (XIII) may be prepared by the reaction of an amine of the formula (XVI):

$$H_2N-CH_2CH_2CR_2R_3R_4 \quad (XVI)$$

with a compound of the formula (XVII):

$$R_7O_2C-\underset{Q}{\underset{|}{CH}}-(CH_2)_nCO_2R_1 \quad (XVII)$$

where Q is a group readily displaceable by an electron rich group.

Suitable groups Q include I, Br, Cl, $O.SO_2.CH_3$, $O.SO_2C_6H_4CH_3$ and other conventional groups.

The displacement reaction occurs under conventional reaction conditions, for example, in an alcoholic solvent in the presence of $Na_2CO_3$ or pyridine.

When $R_2$ is hydrogen or lower alkyl then the amine (XVI) can be prepared by conventional methods. However when $R_2$ and $R_4$ are higher alkyl or cyclic groups as defined in formula (I), then the amine is best prepared by the following reaction scheme, or a scheme chemically analogous thereto:

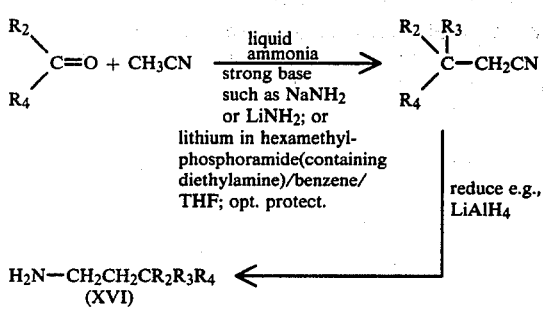

Compounds within the formula (I) have useful pharmacological activity. For example compounds within the formula (I) have anti-gastric secretion activity, cardiovascular activity e.g. anti-hypertensive activity, platelet aggregration inhibition activity, affect the respiratory tract e.g. bronchodilator activity, and have anti-fertility and smooth muscle activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents; for example syrup, acacia, gelatin, sorbitol, tragacanth, or polyvinylpyrrolidone; filler, for example lactose, sugar, maizestarch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additivies such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The compounds of the formula (I) may also if desired be incorporated in a food-stuff, for example in the form of a biscuit.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactantor wetting agent is included in the composition to facilitate uniform distribution of the compound.

When appropriate, the compositions of this invention may be presented for aerosol or oral administration, or as a microfine powder for insufflation.

As is common practice, the compositions will usually be accompanied by written or printed directions for use in the medical treatment concerned.

It has been found that a number of the compounds of the formula (I) are potent inhibitors of gastric secretion, and thus have commercial utility as anti-ulcer agents. In treatment of this nature, the composition containing the formula (I) will preferably be formulated in a manner to allow oral administration. Normally 0.01 mg/kg to 500 mg/kg per day, most suitably 0.1 to 100 mg/kg per day, of the compound of the formula (I) in composition form will be administered in such treatment.

Also a number of compounds of the formula (I) have particularly useful activity on the respiratory tract, and thus find utility as for example bronchodilators. Normally compositions containing such compounds of the formula (I) will be formulated for aerosol or oral administration, or as a microfine powder for insufflation, and the treatment will comprise the administration of from 0.001 mg/kg to 100 mg/kg per day of the compound in composition form.

Further, a number of compounds of the formula (I) are particularly potent inhibitors of platelet aggregation, and thus compositions containing such compounds are useful inter alia for administration to humans and animals to prevent clot formation for example after surgery to prevent postoperative thrombosis; in geriatric patients to prevent transient cerebral ischemic attacks; and long-term prophylaxis following myocardial infarcts and strokes—and in general in the treatment or prophylaxis of any disorder caused by an over pronounced tendency of blood platelets to aggregate. Such compositions also have applications in the storage of whole blood in blood banks, and whole blood to be used in heart-lung machines, or to be circulated through organs, e.g. heart and kidneys, which have been removed from a cadaver and prior to transplant.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or propylaxis of disorders in human beings which comprises the administration to the sufferer of an effective amount of a compound of the formula (I).

It will be realised that when the compound of the formula (I) exhibits platelet aggregation inhibition activity then the invention also provides a method of inhibiting such aggregration in vitro.

It will also be realised that when a compound of formula (I) exhibits anti-fertility activity, then the invention also provides a method of preventing pregnancy comprising the administration to the person or animal of an effective amount of the compound of the formula (I).

The following Examples illustrate the preparation of compounds of the formula (I) and their pharmacological properties.

The organic fractions were combined, dried over magnesium sulphate and evaporated in vacuo to give 3-methyl-1-(N,N-dibenzylamino)-5-phenyl-pentan-3-ol as a yellow oil (75.6 g).

---

I.R. spectrum broad OH absorption at 3330 cm$^{-1}$.
absence of carbonyl absorption.

---

The compounds shown in Table 1 were similarly prepared.

Table 1

$$(PhCH_2)_2NCH_2CH_2 \underset{HO}{\overset{CR_4}{\diagup\!\!\!\diagdown}} CH_3$$

| Compound | Precursor | $R_4$ | OH absorption (cm$^{-1}$) |
|---|---|---|---|
| 1 | Bromobenzene | $C_6H_5$ | 3300 |
| 2 | Benzyl bromide | $CH_2C_6H_5$ | 3300 |
| 3 | 1-Bromo-3-phenyl propane | $(CH_2)_3C_6H_5$ | 3300 |
| 4 | β-Bromo-isopropyl benzene | $CH_2CH(CH_3)C_6H_5$ | 3330 |
| 5 | 2-Bromoethyl-4'-fluorobenzene | $(CH_2)_2$—⟨C$_6$H$_4$⟩—F | 3350 |
| 6 | 1-Bromo-3-(2'-methoxyphenyl)-propane | $(CH_2)_3$—⟨C$_6$H$_4$-OCH$_3$⟩ | 3350 |

EXAMPLE 1

N,N-Dibenzyl-2-aminoethyl methyl ketone

Freshly distilled methyl vinyl ketone (70.5 g) was added dropwise with stirring to a solution of dibenzylamine (197 g) in dry ethanol (50 ml) and the mixture was stirred for 30 minutes.

The solvent was evaporated and the solid residue washed with a small amount of ethanol to give N,N-dibenzyl-2-aminoethyl methyl ketone as a pale yellow solid (211.6 g, 79% yield), m.p. 58°–59°.

N,N-Dibenzyl-2-aminoethyl ethyl ketone was similarly prepared as a yellow oil from ethyl vinyl ketone and dibenzylamine.

---

I.R. spectrum carbonyl absorption at 1700 cm$^{-1}$.
NMR spectrum 10 proton singlet at 2.7τ[(C$_6$H$_5$CH$_2$)$_2$N—]

4 proton broad multiplet at 7.3τ( $\diagdown$N—CH$_2$CH$_2$—)
  $\diagup$ 3 proton triplet at 9.05τ, J = 7cps(—$\underset{\overset{\|}{O}}{C}$CH$_2$CH$_3$)

---

EXAMPLE 2

3-Methyl-1-(N,N-dibenzylamino)-5-phenyl-pentan-3-ol

2-Phenylethyl magnesium bromide was prepared under nitrogen from magnesium (8.04 g) and 2-bromoethyl benzene (54.8 g) in dry tetrahydrofuran (100 ml).

A solution of N,N-dibenzyl-2-aminoethyl methyl ketone (50 g) in dry tetrahydrofuran (200 ml) was added dropwise to the Grignard reagent. The mixture was stirred and refluxed overnight.

A saturated solution of ammonium chloride was added and the product extracted three times with ether.

EXAMPLE 3

1-Amino-3-methyl-5-phenyl-pentan-3-ol

A solution of 3-methyl-1-(N,N-dibenzylamino)-5-phenyl-pentan-3-ol (75.5 g) in ethanol (200 ml) was added to a slurry of 10% Pd/C (8 g) in ethanol. The mixture was hydrogenated at 200 psi and 70° for three days.

The mixture was filtered through kieselguhr and evaporated. The oily produced was fractionally distilled to give 1-amino-3-methyl-5-phenyl-pentan-3-ol as a colourless liquid (15.8 g, 40% yield), b.p. 136°/0.3 mm Hg.

The compounds shown in Table 2 were similarly prepared.

Table 2

$$H_2NCH_2CH_2 \underset{HO}{\overset{CR_4}{\diagup\!\!\!\diagdown}} CH_3$$

| Compound | $R_4$ | B.p. | NH$_2$, OH absorption (cm$^{-1}$) |
|---|---|---|---|
| 7 | $C_6H_5$ | — | 3300 |
| 8 | $CH_2C_6H_5$ | 95°–105°/0.6 mm | — |
| 9 | $(CH_2)_3C_6H_5$ | 130°/0.2 mm | — |
| 10 | $CH_2CH(CH_3)C_6H_5$ | — | 3330 |
| 11 | $(CH_2)_2$—⟨C$_6$H$_4$⟩—F | — | 3350 |

Table 2-continued

H₂NCH₂CH₂CR₄ with HO and CH₃ branches

| Compound | R₄ | B.p. | NH₂, OH absorption (cm⁻¹) |
|---|---|---|---|
| 12 | (CH₂)₃-C₆H₄-OCH₃ | — | 3350 |

EXAMPLE 4

Acetonitrile (7 g) in dry ether (30 ml) was added dropwise to a suspension of sodamide (9.97 g) in liquid ammonia (500 ml). The mixture was stirred for 10 minutes, then a solution of phenylamyl-ketone (30 g) in dry ether (30 ml) was added dropwise. After stirring for an additional hour solid ammonium chloride (14 g) was added. The ammonia was evaporated and during the evaporation ether (50 ml) was added. The residue was treated with water (150 ml) and the ether layer was separated. The aqueous phase was extracted with ether and the combined ether phase was washed with brine until the washings were neutral, then was dried over magnesium sulphate and evaporated in vacuo to give a yellow oil. The unchanged starting materials were removed by vacuum distillation, and the residue which solidified on standing, was reasonably pure 3-hydroxy-3-phenyl-n-octanitrile (12.5 g).

| I.R. spectrum | CN absorption at 2250 cm⁻¹. |
|---|---|
| | OH absorption at 3430 cm⁻¹. |

1-Hydroxy-1-cyanomethyl-cyclohexane, b.p. 101°/0.1 mm was similarly prepared.

EXAMPLE 5

3-Hydroxy-3-phenyl-n-octanitrile (12.45 g) in dry ether (50 ml) was added dropwise to a stirred suspension of lithium aluminium hydride (2.18 g) in dry ether (300 ml). Reflux occurred and this was maintained by external heating for 45 minutes after the final addition. The mixture was cooled (ice-bath) and water (2.5 ml), 15% NaOH solution (2.5 ml) and water (7.5 ml) were added dropwise in sequence. The resulting mixture was stirred for half-an-hour at room temperature, then was filtered through Kieselguhr. The resulting solution was dried over magnesium sulphate, and evaporated in vacuo to give 3-hydroxy-3-phenyl-n-octylamine (12.1 g, 97% crude yield).

| I.R. spectrum | strong absorption 3000–3500 cm⁻¹ due to OH, NH₂ |
|---|---|
| | absence of CN absorption. |

1-Hydroxy-1-(2'-aminoethyl)-cyclohexane, b.p. 81°/0.15 mm, was similarly prepared.

EXAMPLE 6

Diethyl 2-(N-3'-hydroxy-3'-methyl-5'-phenyl-n-pentyl)-aminoazelate

Diethyl 2-bromoazelate (9.7 g) in dry ethanol (50 ml) was added dropwise to a refluxing solution of 1-amino-3-methyl-5-phenyl-pentan-3-ol (5 g) in dry ethanol (150 ml) containing a suspension of anhydrous sodium carbonate (2.7 g). The mixture was refluxed overnight.

The mixture was filtered and the filtrate evaporated in vacuo. The residue was taken up in ether and the ethereal solution was washed with water until the washings were neutral, dried over magnesium sulphate and evaporated in vacuo to give diethyl 2-(N-3'-hydroxy-3'-methyl-5'-phenyl-n-pentyl)-amino-azelate as a pale yellow oil (10.4 g).

| I.R. spectrum | broad OH, NH absorption at 3300 cm⁻¹. |
|---|---|
| | ester carbonyl absorption at 1730 cm⁻¹. |

The compounds shown in Table 3 were similarly prepared:

Table 3

EtO₂C-CH(NH-(CH₂)₂CR₂R₄-OH)-(CH₂)₆CO₂Et

| Compound | R₂ | R₄ |
|---|---|---|
| 13 | CH₃ | C₆H₅ |
| 14 | CH₃ | CH₂C₆H₅ |
| 15 | CH₃ | (CH₂)₃C₆H₅ |
| 16 | CH₃ | CH₂CH(CH₃)C₆H₅ |
| 17 | CH₃ | (CH₂)₂-C₆H₄-F |
| 18 | CH₃ | (CH₂)₃-C₆H₄-OCH₃ |
| 19 | C₆H₅ | C₅H₁₁ |
| 20 | | cyclohexyl |

In each case, the I.R. spectrum showed a broad OH, NH absorption at 0.3300 cm⁻¹ and an ester carbonyl absorption at 1730 cm⁻¹.

EXAMPLE 7

Diethyl 2-[N-3'-hydroxy-3'-methyl-5'-phenyl-n-pentyl)-N-ethoxycarbonylacetyl]-aminoazelate A solution of monoethyl malonate (2.9 g) in dry methylene chloride (50 ml) was added to a solution of diethyl 2-(N-3'-hydroxy-3'-methyl-5'-phenyl-n-pentyl)-aminoazelate (10.4 g) in dry methylene chloride (50 ml). The mixture was stirred at room temperature and a solution of dicyclohexylcarbodiimide (5.0 g) in dry methylene chloride (25 ml) was added dropwise. Stirring was continued overnight.

The mixture was filtered and the filtrate evaporated in vacuo. The residue was taken up in ether and the ethereal solution was washed with dilute hydrochloric acid, sodium bicarbonate solution and then with sodium chloride solution until the washings were neutral. The ether layer was dried over magnesium sulphate and evaporated in vacuo to give diethyl 2-[N-3'-hydroxy-3'-methyl-5'-phenyl-n-pentyl)-N-ethoxycarbonylacetyl]-aminoazelate as a yellow oil (11.9 g).

| I.R. spectrum | broad OH absorption at 3400 cm$^{-1}$.<br>carbonyl absorptions at 1730 cm$^{-1}$ and 1640 cm$^{-1}$. |
| --- | --- |

The compounds shown in Table 4 were similarly prepared.

Table 4

[Structure: EtO$_2$C and EtO$_2$C groups attached to CH with (CH$_2$)$_6$CO$_2$Et chain, N-C(=O)-CH$_2$ linker, and (CH$_2$)$_2$CR$_2$R$_4$ with OH]

| Compound | R$_2$ | R$_4$ |
| --- | --- | --- |
| 21 | CH$_3$ | C$_6$H$_5$ |
| 22 | CH$_3$ | CH$_2$C$_6$H$_5$ |
| 23 | CH$_3$ | (CH$_2$)$_3$C$_6$H$_5$ |
| 24 | CH$_3$ | CH$_2$CH(CH$_3$)C$_6$H$_5$ |
| 25 | CH$_3$ | (CH$_2$)$_2$—C$_6$H$_4$—F |
| 26 | CH$_3$ | (CH$_2$)$_3$—C$_6$H$_4$(OCH$_3$) |
| 27 | C$_6$H$_5$ | C$_5$H$_{11}$ |
| 28 | | cyclohexyl |

In each case, the I.R. spectrum showed a broad OH absorption at 3400 cm$^{-1}$ together with carbonyl absorptions at 1730 cm$^{-1}$ and 1640 cm$^{-1}$.

EXAMPLE 8

2-(6'-Ethoxycarbonyl-n-hexyl)-1-(3''-hydroxy-3''-methyl-5''-phenyl-n-pentyl)-pyrrolidin-3,5-dione Potassium tert-butoxide (2.18 g) was added in small portions over one hour to a warm solution of diethyl 2-[N-(3'-hydroxy-3'-methyl-5'-phenyl-n-pentyl)-N-ethoxycarbonylacetyl]-aminoazelate (11.9 g) in dry toluene (100 ml). The mixture was gently refluxed for 2 hours.

The solvent was evaporated in vacuo and the residue taken up in water. The solution was extracted twice with ether and the aqueous layer was acidified with dilute hydrochloric acid and extracted with ether. This ethereal solution was washed with brine and dried over magnesium sulphate to give a solution of 4-ethoxycarbonyl-2-(6'-ethoxycarbonyl-n-hexyl)-1-(3''-hydroxy-3''-methyl-5''-phenyl-n-pentyl)-pyrrolidin-3,5-dione. The product decarboxylated on standing in ether solution overnight. The solvent was evaporated in vacuo to give 2-(6'-ethoxycarbonyl-n-hexyl)-1-(3''-hydroxy-3''-methyl-5''-phenyl-n-pentyl-pyrrolidin-3,5-dione as a yellow oil (4.7 g).

| I.R. spectrum | broad OH absorption at 3430 cm$^{-1}$.<br>carbonyl absorptions at 1760 cm$^{-1}$, 1720 cm$^{-1}$ and 1680 cm$^{-1}$. |
| --- | --- |

The compounds shown in Table 5 were similarly prepared.

Table 5

[Structure: pyrrolidine-3,5-dione ring with (CH$_2$)$_6$CO$_2$Et substituent at 2-position and N-(CH$_2$)$_2$CR$_2$R$_4$ with OH group]

| Compound | R$_2$ | R$_4$ | OH absorption cm$^{-1}$ | carbonyl absorptions cm$^{-1}$ |
| --- | --- | --- | --- | --- |
| 29 | CH$_3$ | C$_6$H$_5$ | 3400 | 1675, 1720, 1760 |
| 30 | CH$_3$ | CH$_2$C$_6$H$_5$ | 3400 | 1675, 1720, 1760 |
| 31 | CH$_3$ | (CH$_2$)$_3$C$_6$H$_5$ | 3400 | 1675, 1720, 1760 |
| 32 | CH$_3$ | CH$_2$CH(CH$_3$)C$_6$H$_5$ | 3450 | 1680, 1720, 1760 |
| 33 | CH$_3$ | (CH$_2$)$_2$—C$_6$H$_4$—F | 3450 | 1680, 1725, 1765 |
| 34 | CH$_3$ | (CH$_2$)$_3$—C$_6$H$_4$(OCH$_3$) | 3400 | 1680, 1720, 1760 |
| 35 | C$_6$H$_5$ | C$_5$H$_{11}$ | 3400 | 1675, 1725, 1760 |
| 36 | | cyclohexyl | 3450 | 1680, 1725, 1760 |

EXAMPLE 9

2-(6'-Ethoxycarbonyl-n-hexyl)-3-hydroxy-1-(3''-hydroxy-3''-methyl-6''-phenyl-n-hexyl)-pyrrolidin-5-one Sodium borohydride (290 mg) was added portionwise to a solution of 2-(6'-ethoxycarbonyl-n-hexyl)-1-(3''-hydroxy-3''-methyl-6''-phenyl-n-hexyl)-pyrrolidin-3,5-dione (2.5 g) in dry ethanol (50 ml). The mixture was stirred at room temperature for 2 hours.

The solvent was evaporated in vacuo and the residue was taken up in ether. The ethereal solution was washed with very dilute hydrochloric acid and with water, dried over magnesium sulphate, and evaporated in vacuo to give a colourless oil. The product was purified by column chromatography to give 2-(6'-ethoxycarbonyl-n-hexyl)-3-hydroxy-1-(3''-hydroxy-3''-methyl-6''-phenyl-n-hexyl)-pyrrolidin-5-one as a colourless oil (1.5 g, 60% yield).

| I.R. spectrum | broad OH absorption at 3400 cm$^{-1}$. |
| --- | --- |

-continued carbonyl absorptions at 1725 cm$^{-1}$ and 1665 cm$^{-1}$.

The compounds shown in Table 6 were similarly prepared.

Table 6

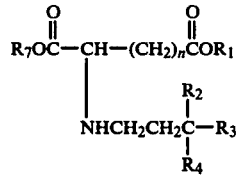

| | | | I.R. spectrum | |
|---|---|---|---|---|
| Compound | $R_2$ | $R_4$ | OH absorption cm$^{-1}$ | carbonyl absorptions cm$^{-1}$ |
| 37 | CH$_3$ | C$_6$H$_5$ | 3400 | 1670, 1720 |
| 38 | CH$_3$ | CH$_2$C$_6$H$_5$ | 3400 | 1670, 1720 |
| 39 | CH$_3$ | (CH$_2$)$_2$C$_6$H$_5$ | 3400 | 1670, 1720 |
| 40 | CH$_3$ | (CH$_2$)$_2$–C$_6$H$_4$–F | 3430 | 1670, 1725 |
| 41 | CH$_3$ | (CH$_2$)$_3$–C$_6$H$_4$–OCH$_3$ | 3400 | 1665, 1725 |

PHARMACOLOGICAL DATA

Anti-secretory activity

The anti-secretory activity of the compounds was determined by their inhibition of pentagastrin-stimulated gastric acid secretion in the perfused rat stomach preparation (Ghosh and Schild preparation). 2-(6'-Ethoxycarbonyl-n-hexyl)-1-(3''-hydroxy-3''-methyl-6''-phenyl-n-hexyl)-pyrrolidin-3,5-dione inhibited acid secretion with an approximate ED$_{50}$ of 850 μg/kg, intravenously.

Inhibition of platelet aggregation

The compounds were examined for their ability to inhibit guinea pig platelet aggregation induced, in vitro, by 5.45×10$^{-7}$ M adenosine diphosphate. 2-(6'-Ethoxycarbonyl-n-hexyl)-1-(3''-hydroxy-3''-methyl-6''-phenyl-n-hexyl)-pyrrolidin-3,5-dione inhibited platelet aggregation with an IC$_{50}$ of 1.6×10$^{-5}$ M.

Bronchodilation activity

The compounds were examined for their ability to inhibit 5-hydroxytryptamine-induced bronchoconstriction in the anaesthetised artificially respired guinea pig (Konzett-Rossler preparation). 2-(6'-Ethoxycarbonyl-n-hexyl)-1-(3''-hydroxy-3''-methyl-6''-phenyl-n-hexyl)-pyrrolidin-3,5-dione inhibited bronchoconstriction with an IC$_{50}$ of 137 μg/kg, intravenously.

Antifertility activity

The antifertility activity of the compounds was determined by their ability to inhibit pregnancy in mated hamsters. 2-(6'-Ethoxycarbonyl-n-hexyl)-3-hydroxy-1-(3''-hydroxy-3''-methyl-5''-phenyl-n-pentyl)-pyrrolidin-5-one completely inhibited pregnancy in hamsters when dosed at 25 mg/kg, subcutaneously, on days 6, 7 and 8 after mating.

Toxicity

No apparent side effects were observed after administration of 2-(6'-ethoxycarbonyl)-n-hexyl)-1-(3''-hydroxy-3''-methyl-6''-phenyl-n-hexyl)-pyrrolidin-3,5-dione at 100 mg/kg subcutaneously in the hamster and I.D. in the rat.

What we claim is:

1. A compound of the formula:

$$R_7OC(=O)-CH(-(CH_2)_nCOR_1)-NHCH_2CH_2C(R_2)(R_3)-R_4$$

wherein n has a value of 4 to 8;
each of R$_1$ and R$_7$ is hydrogen or the residue of an alcohol R$_1$OH or R$_7$OH containing 1 to 12 carbon atoms;
R$_2$ when taken independently of R$_4$ is hydrogen or alkyl of 1 to 4 carbon atoms;
R$_3$ is hydroxy, acyloxy of 1 to 4 carbon atoms or benzyloxy;
R$_4$ when taken independently of R$_2$ is alkyl of 1 to 6 carbon atoms substituted with cycloalkyl of 5 to 8 carbon atoms, phenyl or naphthyl; cycloalkyl of 5 to 8 carbon atoms; phenyl; or naphthyl; any of said phenyl or naphthyl groups being unsubstituted or substituted with halo, trifluoromethyl, alkyl of 1 to 6 carbon atoms, alkoxy of 1 to 6 carbon atoms or nitro; or
R$_2$ and R$_4$ together with the carbon atom to which they are attached are cycloalkylidene of 5 to 8 carbon atoms.

2. A compound according to claim 1 wherein R$_1$ and R$_7$ are each alkyl of 1 to 6 carbon atoms and R$_3$ is hydroxy.

3. A compound according to claim 2 wherein n is 6.

4. A compound according to claim 3 wherein R$_2$ is methyl.

5. A compound according to claim 4 wherein R$_4$ is phenyl.

6. A compound according to claim 4 wherein R$_4$ is benzyl.

7. A compound according to claim 4 wherein R$_4$ is 3-phenylpropyl.

8. A compound according to claim 4 wherein R$_4$ is 2-phenylpropyl.

9. A compound according to claim 4 wherein R$_4$ is 4-fluorophenethyl.

10. A compound according to claim 4 wherein R$_4$ is 2-methoxyphenethyl.

11. A compound according to claim 4 wherein R$_4$ is phenethyl.

12. A compound according to claim 3 wherein R$_2$ and R$_4$ together with the carbon atom to which they are attached are cyclohexylidene.

* * * * *